(12) United States Patent
Wingfield, III et al.

(10) Patent No.: US 6,342,186 B1
(45) Date of Patent: Jan. 29, 2002

(54) CERAMIC LINER FOR CLOSED BOMB APPLICATIONS

(75) Inventors: Horace L. Wingfield, III, Longview; David R. Dillehay, Marshall, both of TX (US)

(73) Assignee: Cordant Technologies Inc., Salt Lake City, UT (US)

( * ) Notice: Subject to any disclaimer, the term of this patent is extended or adjusted under 35 U.S.C. 154(b) by 0 days.

(21) Appl. No.: 08/097,662

(22) Filed: Jul. 26, 1993

(51) Int. Cl.[7] .............................. B01L 3/00; F42B 33/00
(52) U.S. Cl. ...................... 422/102; 422/51; 422/240; 422/241; 436/155; 374/36; 374/37; 374/38; 374/208; 86/50
(58) Field of Search ..................... 89/36.01, 36.02; 86/50; 374/36.37, 38, 208; 422/51, 102, 240, 241; 436/155

(56) References Cited

U.S. PATENT DOCUMENTS

| | | | | |
|---|---|---|---|---|
| 3,765,300 A | * | 10/1973 | Taylor et al. ............... | 89/36 A |
| 3,880,575 A | * | 4/1975 | Cross et al. ................ | 431/353 |
| 4,011,115 A | * | 3/1977 | Harris et al. ................ | 149/22 |
| 4,380,896 A | * | 4/1983 | Wiebe ....................... | 60/39.32 |
| 4,389,947 A | * | 6/1983 | King et al. ................. | 109/1 S |
| 4,419,971 A | * | 12/1983 | Nakamura et al. ......... | 123/193 C |
| 4,524,498 A | * | 6/1985 | Hartsock .................... | 29/156.4 |
| 4,876,941 A | * | 10/1989 | Barnes et al. .............. | 89/36.02 |
| 5,063,881 A | * | 11/1991 | Kawamura ................. | 123/1 A |
| 5,137,789 A | * | 8/1992 | Kaushal ..................... | 428/472 |
| 5,173,229 A | * | 12/1992 | Miyamoto ................. | 264/59 |

OTHER PUBLICATIONS

David R. Dillehey, "Closed Bomb Testing at Longhorn Army Ammunition Plant." pp. 107–122.*

* cited by examiner

Primary Examiner—Harold Pyon
(74) Attorney, Agent, or Firm—Sullivan Law Group

(57) ABSTRACT

Ceramic liners for use with closed bomb devices are disclosed. The closed bomb devices measure performance properties of energetic materials, such as solid propellant, explosive, and pyrotechnic formulations. The closed bomb devices include a body and a ceramic liner. Alumina silicate and boron nitride are two currently preferred ceramic liner materials which have low compressibility, low thermal conductivity, and excellent durability.

18 Claims, 2 Drawing Sheets

CERAMIC LINER FOR CLOSED BOMB APPLICATIONS

BACKGROUND OF THE INVENTION

1. Field of the Invention

This invention relates to apparatus for measuring properties of energetic materials. More specifically, the present invention relates to ceramic liners for use in closed bomb testing of energetic materials such as propellant, explosive, and pyrotechnic formulations.

2. Technology Background

It is often desirable to evaluate the effects of raw materials and processing variables on the functioning of energetic materials. In most cases, it is impractical to manufacture full scale items and test them under field conditions. Closed bomb testing was developed in the early 1960's to provide a low cost, rapid, and effective alternative to full scale testing.

Closed bomb testing was initially used in the development of process controls for rocket propellant manufacturing. The intent was to determine ballistic characteristics of the propellant before it was cast into the motor case. Closed bomb testing is now routinely used for other energetic materials such as pyrotechnic and explosive compositions.

A typical closed bomb device has been prepared by modifying a Parr oxygen bomb calorimeter. The inlet and outlet are modified to allow prepressurization of the bomb with an inert gas and to permit attachment of a strain gage transducer for measurement of pressure-time data. Means for igniting the energetic material is also provided. To reduce thermal loss, the interior of the bomb is lined with silicone rubber. A primer is used on the metal bomb body and the silicone rubber is applied to the bomb interior and cured. The bomb head is also lined with the rubber.

It will be appreciated that any vessel with the required pressure rating can be adapted to closed bomb testing by providing an inlet/outlet for pressurization, a pressure measuring device such as a transducer, and a means for igniting the sample energetic material.

In practice, the bomb is pressurized with an inert gas, such as argon. The energetic material is ignited and the pressure change over time is measured. The burn rate is then calculated from the pressure data by dividing the sample thickness by the apparent burn time (the time from ignition peak to maximum pressure). When the burn rate is plotted against the pre-load pressure on a logarithmic scale, the slope equals the burn rate exponent. Impetus, the work a propellant can do in ft-lb/lb, may also be determined from the pressure data, and the characteristic velocity of a propellant can be related to its impetus.

Impetus values are useful in determining the available energy in a propellant or pyrotechnic. When the impetus is known, it is possible to calculate the maximum pressure in a given volume from the combustion of a known weight of sample. Using the impetus value, the actual hazard of an accidental ignition can be reasonably assessed. For example, when an energetic composition is ignited, the only danger may be from a slow thermal energy release with little danger of over-pressurization and explosion. In other cases, relatively small amounts of composition may produce a rapid pressure build-up that will result in a violent explosion.

To obtain accurate pressure data, it is highly desirable to operate a closed bomb under adiabatic conditions (no heat loss to surroundings). As mentioned above, silicone rubber has been used as an internal liner in an effort to obtain adiabatic conditions.

Silicone rubber, however, has several significant disadvantages. For example, silicone rubber is compressible. Because the test results are based upon a constant volume system in which the actual volume is known, compression of the liner alters the volume and introduces error into the test results. To compensate for such errors, various assumptions and empirical corrections are made to the resulting data in an attempt to make the results look normal.

Other disadvantages of silicone rubber liners are the necessity to cast the liner and the difficulty of bonding the liner to the bomb walls. To apply the silicone rubber liner, the bomb is spun on a lathe and a uniform layer of the silicone rubber is manually placed on the interior surface of the bomb. The bomb is then spun at high rpm under a heat lamp for several hours to cure the rubber. To help the silicone adhere to the bomb interior, a primer coating is often applied. Nevertheless, the silicone liner often peels off of the bomb interior after a few shots. Because a large number of shots are required to obtain data on a single energetic material, the gradual deterioration of the silicone liner over time makes it difficult to obtain reproducible data.

Another major problem associated with silicone rubber liners is the poor durability of the liner, necessitating frequent replacement. The silicone liners degrade in the energetic environment within the closed bomb. After several shots, the liners need to be replaced. Finally, current silicone rubber liners allow significant amounts of heat loss which introduces errors into calculations and makes it more difficult to correlate the measured data.

Accordingly, it would be an advancement in that art to provide closed bomb devices for measuring properties of energetic materials having liners which have low compressibility, low thermal conductivity, and high durability.

Closed bomb devices for measuring performance properties of energetic materials having such liners are disclosed and claimed herein.

SUMMARY OF THE INVENTION

The invention is directed to the use of a ceramic liner in closed bomb devices for measuring performance properties of energetic materials. Alumina silicate and boron nitride are two currently preferred ceramic materials which have low compressibility and low thermal conductivity. These ceramic materials may be machined such that the liner can be accurately and conveniently prepared to fit within the closed bomb device. It has been found that these ceramic materials have excellent durability. The term energetic materials, as used herein, includes solid propellant, explosive, and pyrotechnic formulations.

BRIEF DESCRIPTION OF THE DRAWINGS

In order that the manner in which the above-recited and other advantages and features of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE INVENTION

The present invention is directed to the use of a ceramic liner in closed bomb devices for measuring performance properties of energetic materials. A ceramic liner has several significant advantages over current silicone rubber liners. For example, ceramic liners have low compressibility and low thermal conductivity. This facilitates determination of the bomb volume and permits accurate pressure measurement within the closed bomb device.

Another important advantage of ceramic liners is the ability to machine ceramic materials so that the liner can be press fit within the closed bomb device rather than cast in situ like silicone rubber. For example, if the closed bomb has an interior diameter of 3.000 inches, the ceramic liner may be machined to an exterior diameter of 2.995 inches such that the liner may be press fit into the closed bomb. The heat generated while testing energetic materials will cause the ceramic liner to expand slightly forming a very tight fit within the closed bomb.

Suitable ceramic materials used as a liners preferably have a low thermal conductivity to prevent heat loss to the surroundings. Ceramic materials having a thermal conductivity lower than about 8 BTU·inch/hour·° F.·ft$^2$ are preferred. Because the liners are exposed to high pressures within the closed bomb device, the ceramic liners preferably have a compression strength of at least 35,000 psi. Many energetic materials tested in closed bomb devices generate high temperatures, so it is important that the ceramic liner may be continuously used at a temperature greater than 2000° F. Suitable liners preferably have high flexural strength (10,000 psi minimum) for good resistance to thermal shock. It is also important to have a low thermal expansion coefficient (<2%) to prevent liner cracking during heat treating.

Currently preferred ceramic materials used to prepare the liner include alumina silicate and boron nitride because of their low compressibility and low thermal conductivity. It has been found that these ceramic materials have excellent durability. They may be used for several hundred shots without being replaced.

The closed bomb within the scope of the present invention is used by pressurizing the interior with an inert gas, preferably argon. The energetic material within the bomb is ignited and the pressure change within the closed bomb over time is measured. The burn rate and burn rate exponent are then calculated from the pressure data. Impetus and propellant velocity are also determined from the pressure data according to known techniques.

Figure 1:
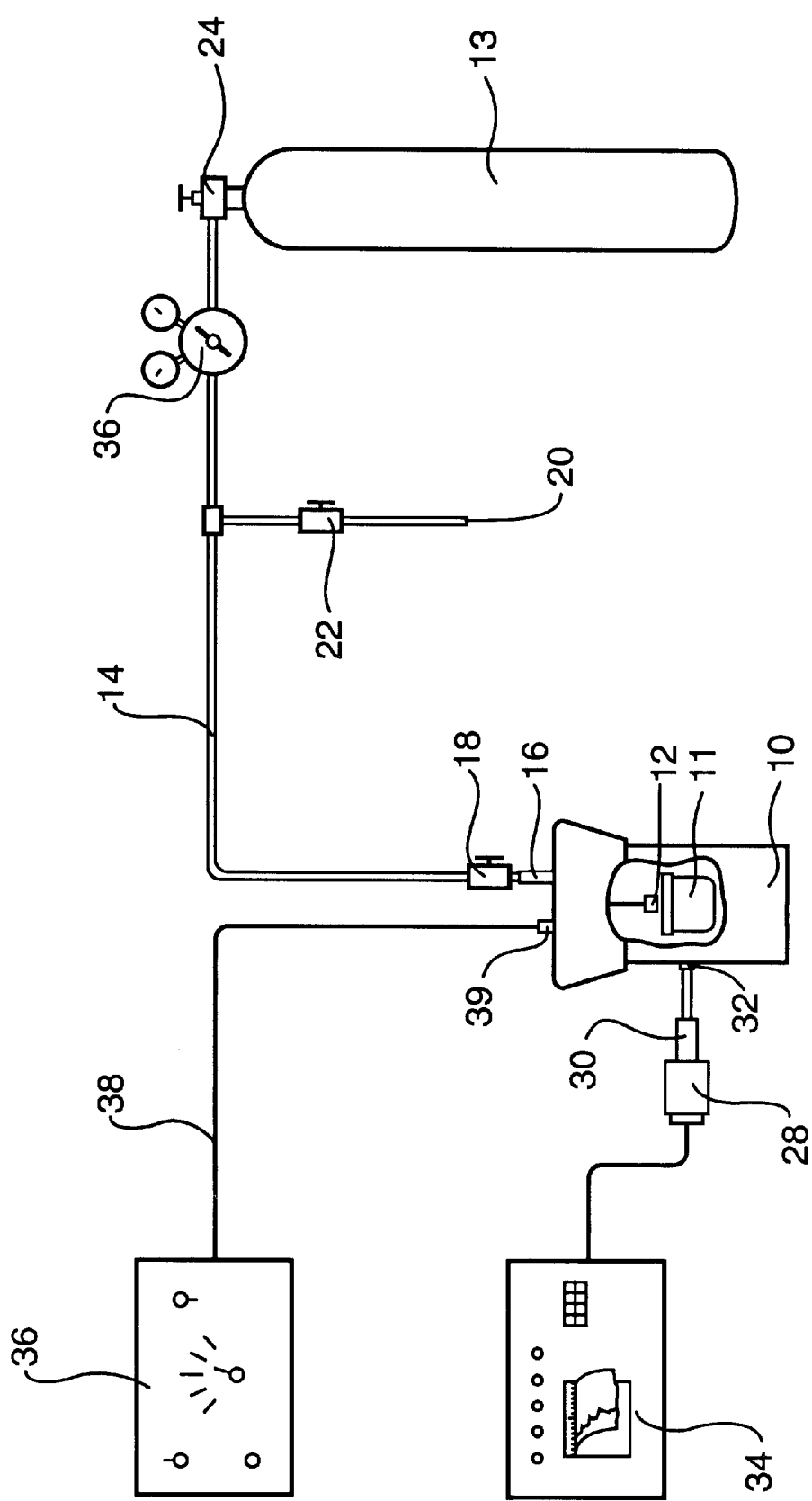
FIG. 1 is a schematic representation of a closed bomb system for measuring properties of energetic materials.

Referring now to FIG. 1, a closed bomb system is illustrated. The closed bomb system includes a closed bomb device, designated generally at 10. Within the interior of the closed bomb device 10 is a ceramic liner (shown in FIG. 2). As shown in partial break-away in FIG. 1, an energetic material holder 11 and an igniter 12 for igniting the energetic material within holder 11 are located within the closed bomb device 10. Typical energetic materials which may be tested within the closed bomb devices of the present invention include solid propellants, explosives, and pyrotechnic formulations. The igniter may be a conventional or novel igniter known to those skilled in the art. Typical igniters which have been used successfully in closed bomb applications include a boron/potassium nitrate and filter paper igniter as well as commercially available squib made by Holex Corp. The squib has a bridge wire igniter and a small charge of black powder held in place by a thin metal disk.

Connected to the closed bomb device 10 is means for pre-pressurizing the closed bomb with an inert gas. As shown in FIG. 1, the means for pre-pressurizing the closed bomb with an inert gas includes an inert gas source 13. Connecting the inert gas source 13 with the closed bomb device 10 is an inert gas line 14 and an inert gas inlet 16 to the closed bomb device 10. A valve 18 is located in the inert gas line 14 close to the inert gas inlet 16 to reduce possible resonance in the inert gas line which might distort pressure measurements within the closed bomb device 10.

The inert gas line 14 includes a vent 20 located between the inert gas source 13 and valve 18 for bleeding the inert gas line when necessary. A vent valve 22 is located adjacent the vent 20 for controlling gas flow out vent 20. The inert gas pressure is controlled by a pressure valve 24 located adjacent the inert gas source 13. The pressure is monitored by pressure meter 26 located within inert gas line 14.

Also connected to the closed bomb device 10 is means for measuring the pressure within the closed bomb device. As shown in FIG. 1, the means for measuring the pressure within the closed bomb device includes a strain gauge transducer 28. It will be appreciated that other pressure measuring devices known to those skilled in the art may also be used. The strain gauge transducer 28 is connected to the closed bomb device 10 through a short pressure line 30 and a pressure outlet 32. The pressure line 30 is preferably filled with grease to eliminate gas flow in the line and possible resonance which might distort pressure measurements. Means for recording pressure-time data is electronically connected to transducer 28. As shown in FIG. 1, the means for recording pressure-time data is an oscillograph 34. Those skilled in the art will appreciate that the transducer 28 may be connected to other data recording devices, including computers.

Means for controlling the energetic material ignition 36 is connected to the closed bomb device 10 through an igniter line 38. As shown in FIG. 1, the igniter line enters the closed bomb device through an igniter port 39 and is connected to igniter 12 located within the closed bomb device which is capable of igniting a sample of energetic material. Various means for controlling ignition of the energetic material known to those skilled in the art may be used, including electronic firing control circuits.

Figure 2:
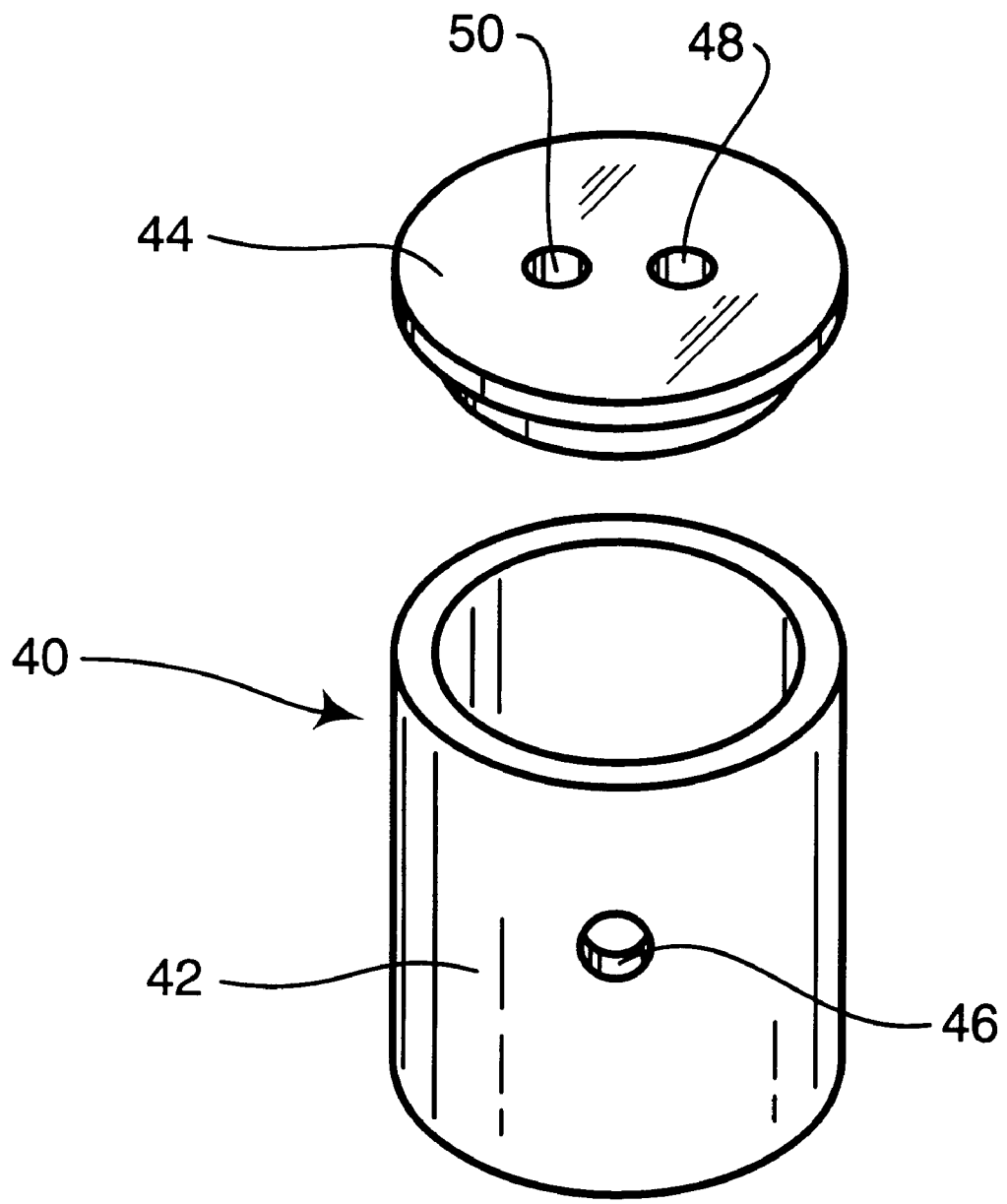
FIG. 2 is a perspective view of a typical ceramic liner for use in a closed bomb device.

Referring now to FIG. 2, ceramic liner 40 is illustrated. The ceramic liner 40 includes a ceramic body 42 and a ceramic lid 44. The body 42 and lid 44 are machined to fit within a closed bomb device, such as that illustrated schematically in FIG. 1 and designated 10. The ceramic liner preferably includes three openings to allow pre-pressurization with an inert gas, pressure monitoring, and igniter control means. As shown in FIG. 2, a pressure opening 46 is located in body 42 to allow the pressure within the closed bomb to be monitored. The lid 44 includes an inert gas opening 48 to allow the closed bomb to be pre-pressurized with an inert gas. The lid 44 also includes an igniter opening 50 to control the igniter operation. It will be appreciated that the location and configuration of the various openings in the ceramic liner may be modified by those skilled in the art to conform to those of the closed bomb device.

From the foregoing it will be appreciated that the present invention provides ceramic liners for closed bomb devices which have low compressibility, low thermal conductivity, and high durability.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A closed bomb device for measuring performance properties of energetic materials comprising a body and a ceramic liner, said ceramic liner having a thermal conductivity lower than about 8 BTU inch/hour·° F.·ft$^2$.

2. A closed bomb device as defined in claim 1, wherein the ceramic liner has a compression strength of at least 35,000 psi.

3. A closed bomb device as defined in claim 1, wherein the ceramic liner may be continuously used at a temperature greater than 2000° F.

4. A closed bomb device as defined in claim 1, wherein the ceramic liner comprises alumina silicate.

5. A closed bomb device as defined in claim 1, wherein the ceramic liner comprises boron nitride.

6. A closed bomb device as defined in claim 1, wherein the energetic material is a solid propellant formulation.

7. A closed bomb device as defined in claim 1, wherein the energetic material is a pyrotechnic formulation.

8. A closed bomb device as defined in claim 1, wherein the energetic material is an explosive formulation.

9. A closed bomb device for measuring performance properties of energetic materials comprising a pressurizable container having an opening for receiving an inert gas, means for igniting a quantity of energetic material, and a pressure port connected to means for measuring pressure changes within said pressurizable container, said pressurizable container having a ceramic liner.

10. A closed bomb device as defined in claim 9, wherein the ceramic liner comprises alumina silicate.

11. A closed bomb device as defined in claim 9, wherein the ceramic liner comprises boron nitride.

12. A closed bomb device as defined in claim 9, wherein the energetic material is a solid propellant formulation.

13. A closed bomb device as defined in claim 9, wherein the energetic material is a pyrotechnic formulation.

14. A closed bomb device as defined in claim 9, wherein the energetic material is an explosive formulation.

15. A closed bomb system for measuring performance properties of energetic materials comprising:

a pressurizable container comprising:
an opening for receiving an inert gas;
an igniter for igniting an energetic material;
a pressure port; and
a ceramic liner;

means for measuring pressure changes within said pressurizable container connected to the pressure port;

means for recording the measured pressure changes within the pressurizable container electronically connected to the means for measuring pressure changes;

a pressurized inert gas source in gaseous communication with the pressurizable container, said gaseous communication being provided through the opening for receiving the inert gas; and means for controlling the operation of the igniter.

16. A closed bomb system as defined in claim 15, wherein the ceramic liner comprises alumina silicate.

17. A closed bomb system as defined in claim 15, wherein the ceramic liner comprises boron nitride.

18. A closed bomb system as defined in claim 15, wherein the pressurized inert gas is argon.

* * * * *